(12) United States Patent
Miller

(10) Patent No.: US 7,074,775 B2
(45) Date of Patent: Jul. 11, 2006

(54) AMINOBUTYRAMIDE CONJUGATE AND A PHARMACEUTICAL COMPOSITION FOR TREATMENT OF NEURONAL DISORDERS

(76) Inventor: Landon C. G. Miller, 325 Queens City Ave., Tuscaloosa, AL (US) 35401

( * ) Notice: Subject to any disclaimer, the term of this patent is extended or adjusted under 35 U.S.C. 154(b) by 0 days.

(21) Appl. No.: 11/023,196

(22) Filed: Dec. 27, 2004

(65) Prior Publication Data

US 2006/0058219 A1 Mar. 16, 2006

Related U.S. Application Data

(60) Provisional application No. 60/609,659, filed on Sep. 14, 2004.

(51) Int. Cl.
| | |
|---|---|
| *A61K 31/70* | (2006.01) |
| *A61K 38/00* | (2006.01) |
| *A61K 38/05* | (2006.01) |
| *A61K 38/16* | (2006.01) |

(52) U.S. Cl. .............. 514/62; 514/2; 514/12; 514/19; 514/23

(58) Field of Classification Search .............. None
See application file for complete search history.

(56) References Cited

U.S. PATENT DOCUMENTS

| | | | | |
|---|---|---|---|---|
| 4,908,353 | A * | 3/1990 | Yamamoto et al. | 514/19 |
| 5,798,337 | A * | 8/1998 | Somers et al. | 514/19 |
| 5,972,924 | A | 10/1999 | Keep et al. | 514/183 |
| 6,241,963 | B1 | 6/2001 | Kung et al. | 424/1.65 |
| 6,403,602 | B1 | 6/2002 | Crooks et al. | 514/282 |
| 6,548,484 | B1 | 4/2003 | Christian | 514/25 |
| 2003/0130205 | A1 | 7/2003 | Christian | 514/23 |
| 2004/0033252 | A1 | 2/2004 | Yamamoto et al. | 424/439 |
| 2004/0142856 | A1 | 7/2004 | DeFrees et al. | 514/8 |
| 2004/0156859 | A1 | 8/2004 | Ezrin et al. | 424/185.1 |

OTHER PUBLICATIONS

"Adjuvant" Stedmans Medical Dictionary, 27th Edition. (2004). accessed Aug. 11, 2005 at http://216.251.232.159/semdweb/internetsomd/ASP/1486797.asp 1 page.*
R. Kassab, et al. Tetrahedron Letters (2000) 41 (6), pp. 877-881.*
N.N. Suvorov, et al. Bioorganicheskaya Khimiya (1976) 2(6), pp. 729-736.*

* cited by examiner

*Primary Examiner*—Bruce R. Campell
*Assistant Examiner*—Andrew D. Kosar
(74) *Attorney, Agent, or Firm*—Gifford, Krass, Groh, Sprinkle, Anderson & Citkowski, P.C.

(57) ABSTRACT

A compound is provided that has the formula $$NH_2CH_2CH_2CH_2C(O)N-R \quad (I)$$

where R is a moiety capable of crossing the blood brain barrier and is as a free compound serotonin, dopamine blood brain barrier (BBB) peptide, membrane translocating protein, TAT peptides, bradykinin, beta-endorphin, bombesin, calcitonin, cholecystokinin, an enkephalin, dynorphin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropin-releasing hormone, growth hormone-releasing hormone, luteinizing hormone, vasoactive intestinal peptidetransferrin, glucosylamnine, amino saccharin, lactylamine, leucine, tryptophan, glutamate and amino cholines.

3 Claims, No Drawings

AMINOBUTYRAMIDE CONJUGATE AND A PHARMACEUTICAL COMPOSITION FOR TREATMENT OF NEURONAL DISORDERS

RELATED APPLICATION

This application claims priority of U.S. Provisional Patent Application Ser. No. 60/609,659 filed Sep. 14, 2004, which is incorporated herein by reference.

FIELD OF THE INVENTION

The subject invention relates to a gamma-aminobutyramide conjugate and synthesis thereof and, more specifically, to the treatment of neuronal disorders by administering the gamma-aminobutyramide conjugate.

BACKGROUND OF THE INVENTION

Gamma-aminobutyric acid (GABA) and glutamic acid are major neurotransmitters which are involved in the regulation of brain neuronal activity. GABA is a major inhibitory neurotransmitter in the mammalian central nervous system. Meythaler et al., *Arch. Phys. Med. Rehabil.* 1999; 80:13–9. Imbalances in the levels of GABA in the central nervous system can lead to conditions such as spastic disorders, convulsions, and epileptic seizures. As described in U.S. Pat. No. 5,710,304, when GABA levels rise in the brain during convulsions, seizures terminate.

GABA is present in an estimated 60 to 70% of all the synapses in the brain (*Med. Sci. Bull.* 1997; 20(5)). There are two types of receptors, GABA-A and GABA-B. The B receptors appear to be involved in spasticity (Meythaler, *Arch. Phys. Med. Rehabil.* 1996; 77(6):628–9; Young, *J. Neurosurg.* 1981; 54(3):300–3), while the A receptors appear to be involved in the control of epilepsy (*Med. Sci. Bull.* 1997; 20(5)). In fact, GABA-A antagonists cause convulsions in animal models (*Med. Sci. Bull.* 1997; 20(5)) as well as spasticity.

Because of the inhibitory activity of GABA and its effect on convulsive states and other motor dysfunctions, the administration of GABA to subjects to increase the GABA activity in the brain has been tried. Because it is difficult to develop and administer a GABA compound which is able to cross the blood brain barrier utilizing systemic administration of GABA compounds, different approaches have been undertaken including making GABA lipophilic by conversion to hydrophobic GABA amides or GABA esters, and by administering activators of L-glutamic acid decarboxylase (GAD). GAD levels vary in parallel with increases or decreases of brain GABA concentration which have been reported to increase GABA levels.

U.S. Pat. No. 4,094,992 to Kaplan et al. discloses benzylidene derivatives which are useful in the treatment of epilepsy and U.S. Pat. No. 4,361,583 to Kaplan discloses the use of the benzylidene derivatives for use in the treatment of pain. This class of drugs are strong GABA agonists which are effective on both GABA-B and GABA-A receptors.

One specific benzylidene derivative disclosed in U.S. Pat. No. 4,094,992 has the chemical structure 4-[[(4-chlorophenyl)-(5-fluoro-2-hydroxyphenyl)methylene]amino]butanamide and is more commonly known as progabide (SL 76002). Progabide does not appear to cause motor weakness in therapeutic dosages to control spasticity and does not appear to significantly affect cognition. There is some suggestion that progabide is an anti-epileptic agent and that it is also neuroprotective. Polasek et al., *Epilepsy Research* 1996; 25:177–84; Kulinskii et al., *Eksperimntalnaia I Klinicheskaia Farmakologiia* 1997; 60:56–8.

As discussed above, there are inherent difficulties in the effective administration of GABA and/or its derivatives to a subject in order to increase brain GABA levels. One of the most pronounced drawbacks of GABA administration is that it does not easily cross the blood brain barrier and, accordingly, does not enter the central nervous system after oral or parenteral administration. The benzylidene derivatives disclosed in the Kaplan et al. patent are considered to be "GABA-mimetic" and are capable of penetrating directly into the brain when administered by oral, endo-rectal, or parenteral routes.

It has been found, however, that, in the brain, when GABA agonists are delivered orally, they may cause some supraspinal activity which may contribute to clinical side effects. For example, for the GABA-B agonist baclofen, it has been found that following oral delivery of the drug that many patients experience central nervous system side effects such as drowsiness, confusion, or memory or attentional problems at the dosages required to reduce spasticity. Young et al., *New Eng. J. Med.* 1981; 304:28–33; Young et al., *New Eng. J. Med.* 1981; 304:96–99; Lazorthes et al., *J. Neurosurg.* 1990; 72:393–402; Sandy et al., *Clin. Neuropharm.* 1985; 8:294–295. Other central nervous system side effects of GABA agonists have included hallucinations, ataxia and memory impairments. Sandy et al., *Clin. Neuropharm.* 1985; 8:294–295; Hattab, *Spasticity, Disordered Motor Control* 1980; Roy et al., *Paraplegia* 1986; 24:318–321. Additionally, the sudden withdrawal of orally delivered GABA compounds may itself lead to seizures and hallucinations. Terrence et al., *Arch. Neurol.* 1981; 38:588–589.

The side effects noted above with the systemic administration of GABA agonists can be largely averted by utilizing intrathecal drug delivery since intrathecal delivery of GABA compounds to the lumbar or mid-thoracic spinal intrathecal space concentrates the medication in the lower area of the spinal cord cerebrospinal fluid at much higher levels than those attainable via the oral route of administration (Meythaler, McCary, Hadley, *J. Neurosurg.* 1997; 87(3):415–9). Typically, the type of delivery system for intrathecal therapy consists of a subcutaneously placed pump having a reservoir which is attached to an intraspinal catheter. This drug delivery methodology concentrates the medication within the spinal subarachnoid space and the thoracolumbar and sacral spinal regions at a much higher level than that attainable via the oral route of administration. Meythaler et al., *J. NeuroSurgery* 1997; 87:415–9. From the subarachnoid space, the cerebrospinal fluid then flows to the arachnoid villi for reabsorption thereby avoiding a significant part of the cerebral hemispheres. Meythaler et al., *Arch. Phys. Med. Rehabil.* 1996; 77:461–466. Only low levels of the medication have the potential to reach the brainstem or cerebrum as studies have demonstrated the lumbar-to-cisternal drug cerebrospinal fluid (CSF) drug concentration gradient is 4.1:1. Kroin et al., *Parenteral Drug Therapy in Spasticity and Parkinson's Disease* 1991, pp. 73–83. By utilizing intrathecal drug delivery, the cognitive side effects of oral drug delivery, such as drowsiness and lethargy, can be avoided. Coffey et al., *J. Neurosurg.* 1993; 78:226–232; Penn et al., *N. Engl. J. Med.* 1989; 320:1517–1522; Knuttson et al., *J. Neurol. Sci.* 1974; 23:473–484. Furthermore, intraventricular delivery does the same for the periventricular area or region of the brain.

Preclinical animal studies in a canine model of the GABA-B agonist, baclofen (2000 µg/d for 28 days), intrathecally through a subcutaneously implanted pump demonstrated no deleterious histopathology in the studied animals. (Sabbe, *Neurotoxicology* 1993; 14(4):397–410). Initial work examining the use of GABA agonists both by systemic delivery and by intrathecal delivery in animal models revealed that baclofen produced a dose dependent analgesia (Bergmann; *Clin. Neuropharcol.* 1985; 8:13–26; Wilson et al., *European J. Pharmacol.* 1978; 51:323–330) and a reduction in motor tone in normal (Bergmann; *Clin. Neuropharcol.* 1985; 8:13–26; Wilson et al., *European J. Pharmacol.* 1978; 51:323–330; Kroin et al., *Exp. Brain Research* 1984; 54:191–194) and genetically spastic animals (Klockgether et al., *Neurosci. Lett.* 1989; 97:221–226).

Based on electrophysiology and the above-discussed preclinical studies, the mechanism of the anti-spasticity associated with intrathecally delivered baclofen is believed to be due to the hyperpolarization of motor horn cells. After the development or onset of upper motor neuron lesions, a variety of long term changes are observed in the brain. Mendell, *Physiological Reviews* 1984; 64(1):260–324. Among these changes, there is an increase in Ia motor unit activity. Wilson et al., *European J. Pharmacol.* 1978; 51:323–330. In humans, while motor horn cells show little change in recurrent inhibition after spinal injury, there is a loss of regulation of Renshaw cell inhibition (Katz et al., *Brain* 1982 March, 105(Pt 1):103–24) and an increased motor neuron excitability (Shemesh et al., *Paraplegia* 1977 November, 15(3):238–44).

Despite the initial success of the intrathecally delivered GABA agonist baclofen in treating the dystonia/spasticity associated with spinal disorders (Meythaler et al., *Arch. Phys. Med. Rehabil.* 1999; 80:13–9; Penn et al., *N. Engl. J. Med.* 1989; 320:1517–1522; Muller et al., *Local-spinal therapy of spasticity* 1988, pp. 223–226), there is still little interest in treating cerebral disorders with intrathecally administered GABA agonists. This lack of interest appears to stem from the lack of success with oral medications in the treatment of dystonia/spasticity resulting from traumatic brain injury (Katz, *Phys. Med. Clin. N. Am.* 1992; 3:319–335; Mann, *J. Neuro. Rehab.* 1991; 5:51–54; Katz, *Am. J. Phys. Med. Rehabil.* 1988; 67:108–116). However, there were indications from some reports that this may be a useful methodology to improve the functional outcome of traumatically brain injured patients. Meythaler et al., *J. NeuroSurgery* 1997; 87:415–9; Meythaler et al., *Arch. Phys. Med. Rehabil.* 1996; 77:461–466. Once clinical trials utilizing programmable infusion pump systems to intrathecally deliver baclofen for the management of dystonia/spasticity in traumatic brain injury were finally initiated, the results were favorable. Meythaler et al., *J. NeuroSurgery* 1997; 87:415–9; Akman et al., *Paraplegia* 1993; 31:516–20. However, not all patients have had a significant sustained response with intrathecally administered baclofen (Meythaler et al., *Arch. Phys. Med. Rehabil.* 1999; 80:13–9), which may be related to its effect only on GABA-B receptors.

Gamma-aminobutyramide appears to bind to both GABA-A and B receptors and it is an excellent candidate for use intrathecally as it is soluble in water and relatively stable for long periods of time. It is able to penetrate from the CNS into the central nervous system. Both the temporal horns and the frontal lobes of the brain are contiguous to the cerebral ventricles which contain CSF. 70% of all seizures are found to be originating in these areas by EEG monitoring. Consequently, intraventricular delivery of gamma-aminobutyramide should be useful in alleviating seizures.

Accordingly, the use of gamma-amninobutyramide, a solubility product of progabide, which is an agonist of both GABA-B receptors and GABA-A receptors, for the treatment of dystonia/spasticity in traumatically brain injured individuals is likely to have a more significant effect. This outcome is indicated by research which indicates that systemically delivered diazepam, a GABA-A receptor agonist, also has profound effects on dystonia and spasticity. Meythaler et al., *Perspectives in Neurosurg.* 1996; 7(2):99–107.

The blood brain barrier is effective in limiting delivery of GABA and gamma-aminobutyramide or (4-aminobutyramide) by systemic routes of delivery. Higher dosages are required to create a therapeutic effect because of poor penetration of the blood brain barrier, the higher dosages also increasing systemic toxicity.

In order to avoid system delivery difficulties, intrathecal and/or cerebral intraventricular administration of gamma-aminobutyramide directly into the cerebrospinal fluid is used to limit systemic toxicity due to the low doses delivered and to the small amount of the chemical or its metabolites that reach the liver from that reabsorbed from the reabsorbed CSF at the arachnoid villi. Additionally, it has been speculated that gamma-aminobutyramide could be useful to reduce spasticity, dystonia, and have effects as an anticonvulsant if its toxicity and systemic delivery issues could be solved. Kaplan et al., *J. Med. Chem.* 1980; 23:702–4.

Thus, there exists a need for an improved composition for systemic and/or intrathecal delivery of gamma-aminobutyramide.

SUMMARY OF THE INVENTION

A compound is provided that has the formula

$$NH_2CH_2CH_2CH_2C(O)N—R \qquad (I)$$

where R is a moiety capable of crossing the blood brain barrier and is as a free compound serotonin, dopamine, blood brain barrier (BBB) peptide, TAT peptides, transferrin, glucosylamine, amino saccharin, lactylamine, leucine, tryptophan, amino glutamate and amino cholines. The compound traverses the blood brain barrier with greater efficiency than gamma-aminobutyramide thereby reducing side effects associated with systemic gamma-aminobutyric acid therapy. A process for forming a conjugate having the formula (I) illustratively includes reacting a butyric acid chloride or ester with a primary or secondary amine group of a transporter molecule able to traverse the blood brain barrier. The transporter molecule includes serotonin, dopamine, blood brain barrier (BBB) peptide, TAT peptide, transferrin, glucosylamine, amino saccharin, lactylamine, leucine, tryptophan, amino glutamate and amino cholines so as to form an amide bond. The amine of the transporter molecule reacts with the butyric acid chloride or ester to form an amide bond.

DETAILED DESCRIPTION OF THE INVENTION

The present invention provides a method for treating neuronal conditions or disorders often associated with traumatic brain injury, including dystonia/spasticity, spastic disorders, convulsive disorders, tardive dyskinesia, pain or epilepsy by administration to a patient or subject having dystonia/spasticity, a spastic disorder, a convulsive disorder, pain or epilepsy a therapeutically effective amount of a gamma-aminobutyramide conjugate that is able to cross the blood-nerve barrier. Adjunct therapies for facilitating such transport are also provided.

The terms "patient" and "subject" are synonymous and mean all animals including humans. Examples of patients or subjects include humans, cows, dogs, cats, goats, sheep, and pigs.

The term "substituted" means that the base organic radical has one or more substituents.

The term "solubility products" means those compounds or compositions formed when a compound is disposed in a solvent.

Those skilled in the art are easily able to identify patients or subjects having dystonia/spasticity, spastic disorders, convulsive disorders, and epilepsy. For example, patients who have sustained traumatic brain injury induced dystonia/spasticity.

A therapeutically effective amount is defined as an amount of gamma-aminobutyramide conjugate that when administered to a patient or subject, ameliorates a symptom of the condition or disorder.

The compounds of the present invention can be administered to a patient either alone or as part of a pharmaceutical composition. The inventive compositions are suitable for administration to patients by a variety of routes including intrathecally, intraventricularly, intravenously, orally, parenterally, and mucosally.

Compositions suitable for delivery illustratively include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers; diluents; solvents; or vehicles include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants.

An inventive compound has the formula

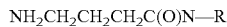　　　(I)

where R is a moiety capable of crossing the blood brain barrier and includes as a separate transporter molecule serotonin, blood brain barrier (BBB) peptide, dopamine, transferrin, TAT peptides, aminated glucose, aminated L-lactate, L-leucine, L-glutamate, aminated saccharin and aminated choline. An inventive compound being formed preferably through the reaction of an acid chloride with a primary or secondary amine in the presence of a tertiary amine present in a stoichiometric excess relative to the quantity of acid chloride. It is appreciated that gamma-aminobutyric acid is an inexpensive starting reagent for coupling by way of an amide linkage to a transporter moiety R. The small size of gamma-aminobutyramide precludes many of the transmembrane transport problems associated with larger molecules.

According to the present invention, a gamma-aminobutyramide conjugate compound is formed to a species known to traverse the blood brain barrier either through diffusion or a specific transporter. While the specific transport mechanism is unclear, owing to the small molecular weight and lack of steric hindrance associated with gamma-aminobutyramide, inhibitory affects on the transporter species associated with conjugation are limited.

In a preferred embodiment, an inventive conjugate compound includes a transporter moiety R having a privileged ability to pass the blood brain barrier and thereafter be cleaved from a gamma-aminobutyramide component to itself form an active therapeutic or neurochemistry equilibrium modifier. The ability to deliver as a conjugate gamma-aminobutyramide with a second neuroactive species provides a previously unavailable ability to moderate a neurological therapeutic effect. As neuroactive compounds are subject to complex feedback mechanisms, the successful transport of a compound across the blood brain barrier has a moderated therapeutic effect owing to neurochemistry equilibrium shifts in response to the compound traversing the barrier. An inventive conjugate provides gamma-aminobutyramide that upon cleavage from the transporter moiety R is in proximity to a second neurologically active species that has an agonistic, antagonistic, or independently operating neuroactive species. The aminobutyramide and moiety R after cleavage being subject to further enzymatic modification and/or efflux clearance. The simultaneous dosage of gamma-aminobutyramide and the neuroactive transporter moiety R upon cleavage assures the desired dose is present. It is appreciated that two or more inventive conjugates are amenable to simultaneous delivery in order to provide still more refined therapeutic affects.

An inventive conjugate compound is preferably formed through an amide linkage between a butyric acid chloride and a primary or secondary aminated blood brain barrier transporter compound. Aminated blood brain barrier transporter compounds operative herein illustratively include serotonin, blood brain barrier (BBB) peptide, membrane translocating protein, dopamine, transferrin, TAT peptides, aminated glucose, aminated L-lactate, L-leucine, L-glutamate, aminated saccharin and aminated choline. The aminated transporter compound is reacted with a butyric acid chloride in the presence of a tertiary amine chloride scavenger in order to form a butyramide having a nitrogen substituent that is able to cross the blood brain barrier. Tertiary amine chloride scavengers operative herein illustratively include pyridine, and trialkyl amines. Alternatively, a butyric acid ester such as a $C_1$–$C_6$ alkyl ester illustratively including ethyl 4 t-BOC-amino-butyrate, and butyl ethyl 4 t-BOC-amino-butyrate.

Carbodiimides are zero length cross-linkers that mediate the formation of an amide or phosphoramidate linkage between a carboxylate and an amine, or a phosphate and an amine, respectively. Chu, B., Kramer, F. & Orgel, L. (1986), "Synthesis of an amplifiable reporter RNA for bioassays," Nucleic Acids Research, 14, 5591–5603. Hoare, D. & Koshland, D. E. (1966) J. Am. Chem. Soc., 88, 2057. Carbodiimides react with carboxylic acids to form highly reactive O-acylisourea compounds that are very short lived but react with nucleophiles to form an amide bond. Dicyclohexylcarbodiimide (DCCD) is representative of a reactive carbodiimde. This reaction works effectively between pH 4.5 and 7.5. Molecules with a phosphate group such as the 5' phosphate on oligonucleotides can also react with amine-containing groups by using the carbodiimide reaction.

Other precursors capable of reacting to form an amide bond are well known to the art. Methods for the preparation of an amide bond are described in Houben-Weyl, Methoden der organischen Chemie (Methods of Organic *Chemistry*), Volume 15/2; Bodanszky et al.

It is appreciated that a butyric acid precursor to an inventive conjugate must include a protected gamma amino group or a moiety that subsequently is reacted to form an amino group yet is unreactive under conditions for the formation of the acid chloride or ester and the subsequent reaction thereof with the aminated transporter compound.

Amine protective groups and the chemistry for the addition thereof to an amino butyric acid are provided in *Protective Groups in Organic Synthesis* by T. W. Greene and P. G. M. Wuts, John Wiley & Sons, 1999 and include the prototypical t-butoxy carbonyl (t-BOC). Alternatively, a moiety such as cyanoalkyl acid is provided as a precursor to form the acid chloride, perform the linkage with the transporter compound, and thereafter reduce the cyano moiety to form the terminal amino group of an inventive conjugate. It is appreciated that other moieties are readily converted to an amine group subsequent to the conjugation chemistry.

Optionally, a linker species is provided intermediate between the transporter moiety R and the aminobutyramide portion of an inventive conjugate. The linker in simplest form includes a moiety reactive with the carbonyl carbon of the butyryl precursor and a second moiety reactive with the transporter compound. Substituents extending from a linker are provided to modify the lipophilicity of an inventive conjugate, or tether a dye or spectroscopic marker. With the inclusion of a linker, care should be taken to limit both the molecular weight and the hydrophilicity of the linker in order to retain the ability to traverse the blood brain barrier. Typically, the linker has eight or less backbone carbon atoms. Preferably, the linker backbone is linked to the butyryl amido portion of an inventive conjugate through an oxygen atom or a carbon atom. The linker moiety reactive with the butyryl portion carbonyl carbon illustratively form an amide and an ester linkage. Transporter compound reactive moiety of the linker is dependent upon the transporter compound moiety to be bound thereto. Suitable chemistries for a variety of potential reaction moieties are found in *Comprehensive Organic Transformations*, R. C. Larock, John Wiley & Sons 1999.

It is appreciated that a linker, when present, is the preferred site for the attachment of an additional species. A substituent is optionally provided pendent from the linker backbone. The substituent illustratively includes a radioactive atom, a magnetic spectroscopically active marker and an organic dye. A radioactive atom is alternatively operative as a marker in isotope studies such as positron emission tomography, single photon emission computer tomography, radiological studies and the like. Common radio-isotopes used in medical imaging illustratively include $^{123}$I, $^{99m}$Tc, and other chelated radioisotopes as detailed in U.S. Pat. No. 6,241,963. Spectroscopically active markers include NMR/MRI active contrast enhancing moieties known to the art such as gadolinium, as detailed in Contrast Agents 1: Magnetic Resonance Imaging (Topics in Current Chemistry, 221) by Werner Krause, Springer Verlag, Berlin, Germany. Organic dyes, while recognized to have potentially distinct NMR/MRI signatures, are provided to yield an optically active spectroscopic signature suitable for biopsy, surgical identification, or preclinical studies of tissue treated by an inventive compound.

Compositions suitable for injection optionally include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied with to a thickness such that the entire coating does not dissolve in the gastrointestinal fluids at pH below 5 associated with stomach acids, yet dissolves above pH 5 in the small intestine environment. It is expected that any anionic polymer exhibiting a pH-dependent solubility profile is readily used as an enteric coating in the practice of the present invention to achieve delivery of the active to the lower gastrointestinal tract. The selection of the specific enteric coating material depends on properties such as resistance to disintegration in the stomach; impermeability to gastric fluids and active agent diffusion while in the stomach; ability to dissapate at the target intestine site; physical and chemical stability during storage; non-toxicity; and ease of application.

Suitable enteric coating materials illustratively include-cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonio methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particularly preferred enteric coating material for use herein are those acrylic acid polymers and copolymers available under the tradename EUDRAGIT®, Roehm Pharma (Germany). The EUDRAGIT® series L, L-30D and S copolymers are most preferred since these are insoluble in stomach and dissolve in the intestine.

The enteric coating provides for controlled release of the active agent, such that release is accomplished at a predictable location in the lower intestinal tract below the point at which drug release would occur absent the enteric coating. The enteric coating also prevents exposure of the active agent and carrier to the epithelial and mucosal tissue of the buccal cavity, pharynx, esophagus, and stomach, and to the enzymes associated with these tissues. The enteric coating therefore helps to protect the active agent and a patient's internal tissue from any adverse event prior to drug release at the desired site of delivery. Furthermore, the coated solid dosages of the present invention allow optimization of drug absorption, active agent protection, and safety. Multiple enteric coatings targeted to release the active agent at various regions in the lower gastrointestinal tract would enable even more effective and sustained improved delivery throughout the lower gastrointestinal tract.

The enteric coating optionally contains a plasticizer to prevent the formation of pores and cracks that allow the penetration of the gastric fluids into the solid dosage. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The enteric coating is applied to a solid dosage using conventional coating methods and equipment. For example, an enteric coating can be applied to a solid dosage using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6.sup.th Ed. (Media, Pa.: Williams & Wilkins, 1995).

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

An inventive compound is also delivered in conjunction with an active therapeutic compound. The therapeutic compound illustratively being active as antibiotic, a gamma or beta radiation emitting species, an anti-inflammatory, an antitumoral, an antiviral, an antibody, a hormone, an enzyme, and antigenic peptide or protein.

The examples presented below are intended to illustrate particular embodiments of the invention and are not intended to limit the scope of the specification, including the claims.

EXAMPLES

Example 1

Preparation of 4-aminobutyramide of Serotonin

Oxalyl chloride (2 mmol, 1 mL from 2 M solution in $CH_2Cl_2$) is added to t-butoxycarbonyl (t-Boc) amine protected 4-aminobutyric acid (1 mmol) in $CH_2Cl_2$ (10 mL) at room temperature under $N_2$. The resulting mixture is stirred for 1.5 hours and concentrated in vacuo at 30° C. to obtain a viscous oil which is dried in a vacuum for 15 minutes. The acid chloride obtained was dissolved in $CH_2Cl_2$ (10 mL) and cooled to −10° C. and serotonin (1 mmol, 175 mg) in $CH_2Cl_2$ (10 mL) is added, followed by triethylamine (3 mmol, 0.42 mL), under $N_2$. The resulting solution is stirred at room temperature for 6 hours. The resulting solution is stirred for 3 hours in trifluoroacetic acid (1 M) to remove the t-Boc group. Water (20 mL) is then added to the reaction mixture and the product is extracted into $CH_2Cl_2$ (3×20 mL). $CH_2Cl_2$ layers are combined, dried and concentrated in vacuo to obtain the inventive conjugate.

Example 2

Preparation of 4-aminobutyramide of N-glucosyl Amine

The preparation of Example 1 is repeated with the substitution of a molar stoichiometric equivalent N-glucosylamine for serotonin, to form the title conjugate.

Example 3

Preparation of 4-aminobutyramide of Dopamine

A mixture of ethyl t-butoxycarbonyl (t-Boc) amine protected 4-aminobutyrate (5 mmol) and dopamine (5 mmol) in 200 ml tetrahydrofuran are heated to 70° C. for 24 hours. The resulting dopaminyl-t-butoxycarbonyl (t-Boc) amine protected 4-aminobutyramide is collected as an oil and stirred for 3 hours in trifluoroacetic acid (1 M) to remove the t-Boc group. Water (20 mL) is then added to the reaction mixture and the product is extracted into THF (3×20 mL). THF layers are combined, dried and concentrated in vacuo to obtain the inventive conjugate.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A compound having the formula:

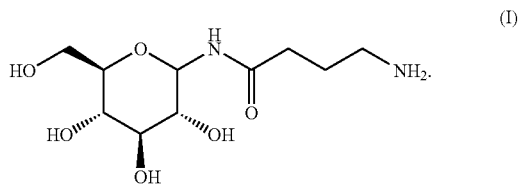

(I)

2. A therapeutic composition comprising the compound of claim 1 in a physiologically suitable solvent for administration by a route selected from the group consisting of: parenteral, intraventricular, and intrathecal.

3. The composition of claim 2 further comprising an adjuvant.

* * * * *